(12) United States Patent
Hatipoglu et al.

(10) Patent No.: US 8,828,453 B2
(45) Date of Patent: Sep. 9, 2014

(54) HERBAL-BASED COMPOSITIONS FOR ALLEVIATING SYMPTOMS ASSOCIATED WITH AUTISM

(76) Inventors: Betul Hatipoglu, Beachwood, OH (US); Randolph Margrave, Daytona Beach, FL (US)

( * ) Notice: Subject to any disclaimer, the term of this patent is extended or adjusted under 35 U.S.C. 154(b) by 152 days.

(21) Appl. No.: 13/097,678

(22) Filed: Apr. 29, 2011

(65) Prior Publication Data

US 2011/0268717 A1 Nov. 3, 2011

Related U.S. Application Data

(60) Provisional application No. 61/329,429, filed on Apr. 29, 2010.

(51) Int. Cl.
*A61K 36/00* (2006.01)

(52) U.S. Cl.
USPC ................................ 424/725; 424/681

(58) Field of Classification Search
USPC .......................................................... 424/725
IPC ............................................................. A61K 36/18
See application file for complete search history.

(56) References Cited

U.S. PATENT DOCUMENTS

| | | | | | |
|---|---|---|---|---|---|
| 5,051,258 | A | * | 9/1991 | Sahley | 424/439 |
| 5,569,459 | A | * | 10/1996 | Shlyankevich | 424/728 |
| 5,681,578 | A | * | 10/1997 | Sahley | 424/439 |
| 2008/0107754 | A1 | * | 5/2008 | Luciano | 424/641 |
| 2008/0213198 | A1 | * | 9/2008 | Lintner et al. | 424/59 |
| 2009/0011015 | A1 | * | 1/2009 | Gardiner et al. | 424/465 |
| 2009/0044499 | A1 | * | 2/2009 | Chambers et al. | 54/49 |
| 2009/0155392 | A1 | * | 6/2009 | Nelson et al. | 424/725 |
| 2009/0202445 | A1 | | 8/2009 | Nieuwenhuijsen | |
| 2009/0304602 | A1 | * | 12/2009 | Tuchinsky | 424/43 |
| 2010/0063161 | A1 | * | 3/2010 | Miller et al. | 514/689 |
| 2013/0015204 | A1 | * | 1/2013 | Gol | 222/129 |

FOREIGN PATENT DOCUMENTS

| | | | |
|---|---|---|---|
| AU | 2009100934 | * | 11/2009 |
| JP | 2009091297 | * | 4/2009 |
| WO | WO 2008/059965 | * | 5/2008 |

OTHER PUBLICATIONS

Abush, H. et al., "Cannabinoids modulate hippocampal memory and plasticity," Hippocampus,20(10):1126-1138 (Oct. 14, 2009).
Alger, B., "Retrograde signaling in the regulation of synaptic transmission: focus on endocannabinoids," Prgo Neurobiol, 68(4):247-286 (Nov. 2002).
Campolongo, R., et al., "Endocannabinoids in the rat basolateral amygdala enhance memory consolidation and enable glucocorticoid modulation of memory," Proc Natl Acad Sci USA, 106(12):4888-4893 (Mar. 14, 2009).
Chakrabarti, B., et al., "Variations in the human cannabinoid receptor (CNR1) gene modulate striatal responses to happy faces," Eur J Neurosci, 23(7):1944-1948 (Apr. 2006).
Chakrabarti, B. et al., "Variations in the human cannabinoid receptor *CNR1* gene modulates gaze duration for happy faces," Mol Autism, 2(10):(7 pages) (2011).
Coyle, J. et al., "Oxidative stress, glutamate, and neurodegenerative disorders," Science, 262(5134):689-695 (Oct. 1993).
Dean, B., et al., "Studies on [$^3$H]CP-55940 binding in the human central nervous system: regional specific changes in density of cannabinoid-1 receptors associated with schizophrenia and cannabis use," Neuroscience, 103(1):9-15 (Feb. 28, 2001).
Devane, W., et al., "Isolation and structure of a brain constituent that binds to the cannabinoid receptor," Science, 258(5090):1946-1949 (Dec. 18, 1992).
Dhawan K., et al., "Reversal of cannabinoids (Δ9-THC) by the benzoflavone moiety from methanol extract of *Passiflora incarnata* Linneaus in mice: a possible therapy for cannabinoid addiction," J Pharm Pharacol, 54(6):875-881 (2002).
Dhawan, K., et al., "Anxiolytic activity of aerial and underground parts of *Passiflora incarnata*," Fitoterapia, 72(8):922-926 (Dec. 2001).
Dhawan, K., et al., "Correct identification of *Passiflora incarnata* Linn., a promising herbal anxiolytic and sedative," J Med Food, 4(3):137-144 (Sep. 2001).
Eshhar, N., et al., "Neuroprotective and antioxidant activities of HU-211, a novel NMDA receptor antagonist," Eur J Pharmacol, 283(1-3):19-29, (Sep. 5, 1995).
Gerdeman, G., et al., "Postsynaptic endocannabinoid release is critical to long-term depression in the striatum," Nat Neurosci, 5(5):446-451 (May 2002).
Glass, M., "The role of cannabinoids in neurodegenerative diseases," Prog Neuropsychopharmacol Biol Psychiatry, 25(4):743-765 (May 2001).
Glass, M., et al., "Cannabinoid receptors in the human brain: a detailed anatomical and quantitative autoradiographic study in the fetal, neonatal and adult human brain," Neuroscience, 77(2):299-318 (Feb. 21, 1997).
Grundmann, O., et al., "Anxiolytic activity of a phytochemically characterized *Passiflora incarnata* extract is mediated via the GABAergic system," Planta Med, 74(15):1769-1773 (2008).
Gulyas, A., et al., "Segregation of two endocannabinoid-hydrolyzing enzymes into pre-and postsynaptic compartments in the rat hippocampus, cerebellum and amygdala," Eur J Neurosci, 20(2):441-458 (Jul. 2004).

(Continued)

*Primary Examiner* — Chris R Tate
(74) *Attorney, Agent, or Firm* — Greenberg Traurig, LLP; Chinh H. Pham; Natalie Salem

(57) ABSTRACT

Aspects of the invention relate to compositions comprising *passiflora* extracts that may improve neurological and behavioral symptoms associated with Pervasive Developmental Disorders.

15 Claims, No Drawings

(56) References Cited

OTHER PUBLICATIONS

Guptill, J., et al., "[$^3$H]-Flunitrazepam labeled benzodiazepine binding sites in the hippocampal formation in autism: a multiple concentration autoradiographic study," Journal Autism Dev Disord., 37(5):911-920 (May 2007).

Herkenham, M., et al., "Cannabinoid receptor localization in brain," Proc Natl Acad Sci USA, 87(5):1932-1936 (Mar. 1, 1990).

Hughes, J., "A review of recent reports on autism: 1000 studies published in 2007," Epilepsy Behav, 13(3):425-437 (Oct. 2008).

Katona, I., et al., "Distributions of CB1 cannabinoid receptors in the amygdala and that role in the control of CABAergic transmission," J Neurosci, 21(23):9506-9518 (Dec. 1, 2001).

Koethe, D., et al., "Expression of CB1 cannabinoid receptor in the anterior cingulate cortex in schizophrenia, bipolar disorder, and major depression," J Neural Transm, 114(8):1055-1063 (Mar. 19, 2007).

Krenn, L., "[Passion flower (*Passiflora incarnata* L.)—an effective sedative herb]," Wien Med Wochenschr, 152(15-16):404-406 (2002).

Leweke, F., et al., "Elevated endogenous cannabinoids in schizophrenia," Neuroreport, 10(8):1665-1669 (Jun. 3, 1999).

Loveland, K., "Fronto-limbic functioning in children and adolescents with and without autism," Neuropsychologia, 46(1):49-62 (Jan. 15, 2008).

Lutz, B., "On-demand activation of the endocannabinoid system in the control of neuronal excitability and epileptiform seizures," Biochem Pharmcaol, 68(9):1691-1698 (Nov. 1, 2004).

Marsicano, G. et al., "Expression of the cannabinoid receptor CB1 in distinct neuronal subpopulations in the adult mouse forebrain," Eur J Neurosci, 11(12):4213-4225 (Dec. 1999).

Masteikova, R., et al., "Antiradical activities of the extract of *Passiflora incarnata*," Acta Pol Pharm, 65(5)577-583 (Sep.-Oct. 2008).

McNamara, J., "Emerging insights into the genesis of epilepsy," Nature, 399(6738 Suppl.):A15-A22 (Jun. 24, 1999).

Mechoulam, R., et al., "Endocannabinoids and neuroprotection," Sci STKE, 2002(129):re5 (Apr. 23, 2002).

Mechoulam, R., et al., "Identification of an endogenous 2-monoglyceride, present in canine gut, that binds to cannabinoid receptors," Biochem Pharmacol, 50(1):83-90 (Jun. 29, 1995).

Monk, C., et al., "Neural circuitry of emotional face processing in autism spectrum disorders," J Physchiatry Neurosci, 35(2):105-114, (Mar. 2010).

Moriera, F. et al., "The endocannabinoid system: emotion, learning and addiction," Addict Biol, 13(2):196-212 (Jun. 2008).

Newell, K., et al., "Increased cannabinoid receptor density in the posterior cingulate cortex in schizophrenia," Exp Brain Res, 172(4):556-560 (May 2006).

Oblak, A., et al., "Decreased $GABA_A$ receptors and benzodiazepine binding site in the anterior cingulate cortex in autism," Autism Res, 2(4):205-219 (Aug. 2009).

Pacher, P., et al., "The endocannabinoid system as an emerging target of pharmacotherapy," Pharmacol Rev, 58(3):389-462 (Sep. 1, 2006).

Piomelli, D., "The molecular logic of endocannabinoid signalling," Nat Rev Neurosci, 4(11):873-884 (Nov. 2003).

"Prevalence of autism spectrum disorders—autism and development disabilities monitoring network, six sites, 2000" MMWR Surveill Summ, 56(1):1-11 (Feb. 9, 2007).

Reich, C., et al., "Endocannabinoid modulation of fear responses: learning and state-dependent performance effects," J Psycholpharmacol, 22(7):769-777 (Sep. 2008).

Schulkin, J., "Autism and the amygdala: an endocrine hypothesis," Brain Cogn, 65(1):87-99 (Aug. 2, 2007).

Shouman, B., et al., "Endocanabinoids potently protect the newborn brain against AMPA-kainate receptor-mediated excitotoxic damage," Br J Pharmacol, 148(4):442-451 (Jun. 2006).

Solinas, M., "The endocannabinoid system in brain reward processes," Br J Pharmacol, 154(2):369-383 (Apr. 14, 2008).

Stigler, K. et al., "Pharmacotherapy of irritability in pervasive development diorders," Child Adolesc Psychiatr Clin N Am, 17(4):739-752 (2008).

Sugiura, T., et al., "2-Arachidonoylglycerol: A possible endogenous cannabinoid receptor ligand in brain," Biochem Biophys Res Commun, 215(1):89-97 (Oct. 4, 1995).

Tabach, R., et al., "Preclinical toxicological assessment of a phytotherapeutic product—CPV (based on dry extracts of *Crataegus oxyacantha* L., *Passiflora incarnata* L., and *Valeriana officinalis* L.), Phytother Res, 23(1):33-40 (Dec. 1, 2008).

Thatcher R., et al., "Autism and EEG Phase Reset: Deficient GABA Mediated Inhibition in Thalamo-Cortical Circuits," Dev Neuropsychol, 34(6):780-800 (Nov. 2009).

Vargas, D., et al., "Neuroglial activation and neuroinflammation in the brain of patients with autism," Ann Neurol, 57(1):67-81 (Nov. 15, 2004).

West, L., et al., "Pharmacologic treatment for the core deficits and associate symptoms of autism in children," J Pediatr Health Care, 23(2):75-89 (Mar.-Apr. 2009).

* cited by examiner

HERBAL-BASED COMPOSITIONS FOR ALLEVIATING SYMPTOMS ASSOCIATED WITH AUTISM

This application claims the priority to U.S. Provisional Application No. 61/329,429, filed Apr. 29, 2010, which application is hereby incorporated by reference in its entirety.

FIELD OF INVENTION

The present invention relates to nutraceutical compositions and methods of administering such for improving neurological functions and behavioral symptoms associated with Pervasive Developmental Disorders. More specifically, the present invention relates to the use of herbal-based compositions having an endocannabinoid agonist-antagonist effect to restore a balance between inhibitory GABAergic pathways and excitatory glutamatergic pathways, often associated with autism.

BACKGROUND

Autism may be defined as a condition, usually present from childhood, that is characterized by self-absorption, a reduced ability to respond to or communicate with the outside world and behavioral dysfunction. An autistic individual may suffer from several maladies with the accumulated symptoms being categorized as autism spectrum disorders, referred to in the field as autism or ASD. Symptoms of autism include stimming, reduced eye contact, perseveration (i.e., repeating same activity for long periods), poor communication and social skills and heightened sound sensitivity, amongst others.

It is estimated that about 1 in 100 children are affected by autism with an initial manifestation of symptoms by age three. Generally, males are more likely to suffer from autism than females. It should be noted that the overall percentage of persons exhibiting symptoms of autism may be increasing, in some instances dramatically. This rise may be due in part to an increase in the percentage of persons receiving childhood vaccinations.

There is a need for the identification of compositions to ameliorate or prevent symptoms associated with Pervasive Developmental Disorders, such as Autism, Asperger disorder and/or Retts disorder.

SUMMARY OF THE INVENTION

The present invention provides, compositions to reduce, ameliorate, treat or alleviate symptoms associated with a Pervasive Developmental Disorder, such as Autism, Asperger disorder and/or Retts disorder by restoring a balance between inhibitory GABAergic pathways and excitatory glutamatergic pathways. In some embodiments, the compositions can be nutraceutical compositions, pharmaceutical compositions, drugs, food supplements, medical foods to improve neurological function in Pervasive Developmental Disorders such as autism, Asperger disorder and Retts disorder.

In an embodiment, the herbal-based compositions have an endocannabinoid agonist-antagonist effect. The composition includes, in one embodiment, a passion flower extract. The passion flower extract may be selected from one of *passiflora incarnate* extract, *passiflora coerulea* extract, *passiflora edulis* or combinations thereof. The composition, in some embodiments, further includes one of magnesium chloride, a water-soluble compound, an oil-soluble substance or combinations thereof. In some embodiments, the composition can include magnesium chloride, vitamin B6, and Coenzyme Q10 (CoQ10).

In some embodiments, the passion flower extract can be present from about 10 mg to about 500 mg. In some embodiments, the *passiflora incarnate* extract is present from about 100 mg to about 500 mg. In some embodiments, the *passiflora coerulea* extract is present from about 50 mg to about 400 mg. In some embodiments, the *passiflora edulis* extract is present from about 10 mg to about 200 mg. In some embodiments, the water-soluble compound is vitamin B6. The vitamin B6 can be present from about 10 mg to about 50 mg. In some embodiments, the oil-soluble substance is co-enzyme Q10. The coenzyme Q10 can be present from about 5 mg to about 100 mg.

Some aspects of the invention relate to a composition for reducing, alleviating, treating, ameliorating symptoms associated with a Pervasive Developmental Disorders. In such embodiments, the composition includes a passion flower extract, magnesium chloride, vitamin B6 and coenzyme Q10. The composition can be suitable for oral administration and can be used to improve neurological function and/or behavioral symptoms in Pervasive Developmental Disorders. The composition can be selected from one of gelatin capsules, caplets compressed into tablets, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, gummie, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables, infusions, health bars, confections, animal feeds, cereals, yogurts, cereal coatings, foods, nutritive foods, functional foods, or a combination thereof. The composition can further include one or more binders selected from the group consisting of microcrystalline cellulose, gum tragacanth, gelatin; starch, lactose, alginic acid, Primogel, corn starch; magnesium stearate, colloidal silicon dioxide, sucrose or saccharin; peppermint, methyl salicylate, orange flavoring, or a combination thereof.

Some aspects of the invention relate to methods comprising providing a composition having a passion flower selected from one of *passiflora incarnate* extract, *passiflora coerulea* extract, *passiflora edulis* or combinations thereof and administering to a subject in need thereof an effective amount of the composition to reduce, treat, ameliorate or alleviate symptoms associated with Pervasive Developmental Disorder. In some embodiments, the composition is formed with one of magnesium chloride, a water-soluble compound, an oil-soluble substance or combinations thereof. In some embodiments, the water-soluble compound is vitamin B6. In some embodiments, the oil-soluble substance is co-enzyme Q10. The composition can be administered orally, topically, intravenously, or by combination thereof. The composition can be administered once daily or in the range from about one to up to eight times or more a day. In some embodiments, the Pervasive Developmental Disorder is autism, Asperger disorder or Retts disorder.

DESCRIPTION OF SPECIFIC EMBODIMENTS

Review of prospective experimental studies of pharmacotherapy conducted in the USA on children between 5 and 15 years reports moderate success in treating the associated maladaptive behaviors of autism and minimal success in treating core deficits across all drug classes. This is due in part to the fact that the etiology of autism is not fully understood. Chromosomal abnormalities in chromosomes 15-17, abnormal genes like MECP 2, central nervous system conditions involving the frontal cortex, amygdalae, hippocampus, and temporal lobe; gray-white volume; abnormal serotonin levels, diminished minicolumns, absence of mirror neurons and various parental conditions have been implied in etiopathogenesis (Hughes J R, Epilepsy Behav. 2008).

Different parts of the brain are involved in executive function, affect, socio-emotional behavior and may experience GABAergic down-regulation. Deficiency of this inhibitory pathway function can be seen in autism. The anterior cingulate cortex (ACC), via its extensive limbic and high order association cortical connectivity to prefrontal cortex, may be a key part of the circuitry involved in executive function, affect, and socio-emotional behavior. Studies, including genetic and imaging studies, suggest that the ACC and gamma-amino-butyric acid (GABA) system may be affected in autism. The benzodiazepine binding site on the GABA (A) receptor complex is an important target for pharmacotherapy and may have important clinical implications. Findings suggest that in the adult autistic brain there may be down regulation of both benzodiazepine sites and GABA (A) receptors in the ACC disturbing the delicate excitation/inhibition balance by favoring excitation of principal neurons as well as their output to key limbic cortical targets via glutamatergic pathway (Oblak et al., Autism. Res., 2009; Guptill et al., J. Autism Dev. Disord., 2007).

Balance between excitation and inhibition are delicately maintained in many parts of the brain. If the balance between inhibition and excitation among neurons is disturbed in favor of the excitatory glutamatergic pathways, the intensity of excitatory transmission may lead to adverse behavioral and neurological consequences. Multiple pathways eventually culminating in neuronal death, are triggered by excessive excitatory activity through a process known as excitotoxicity. Excitotoxicity is believed to contribute to the progression of numerous degenerative central nervous system disorders such as Parkinson's disease and various forms of epilepsy. Excitotocity may also be involved in autism spectrum disorders.

Increased excitatory glutamatergic and decreased inhibitory GABAergic pathways in different parts of the brain may be, in an embodiment, explained by a dysfunctional endocannabinoid system. Stimulation of postsynaptic neurons may trigger the demand synthesis of endocannabinoids by an increase in intracellular calcium and/or stimulation of metabotropic receptors. Subsequently, endocannabinoids may be released and may reach presynaptic CB1 Receptors retrogradely to modulate both inhibitory GABAergic system and excitatory glutamatergic transmissions through multiple mechanisms.

The endocannabinoid system is an emergent neuro-immuno-endocrine connection of the body which first attracted interest with the medicinal uses of marijuana. Cannabinoids, including the bioactive constituents of the marijuana plant, their synthetic analogs, and endogenous lipids with cannabinoid-like activity, produce certain biological effects by interacting with specific receptors. To date, two G protein-coupled cannabinoid receptors have been identified by molecular cloning: CB1 receptors mainly expressed in the brain and mediating most of the neurobehavioral effects of cannabinoids and CB2 receptors expressed by immune and hematopoietic tissues. Recent findings indicate that some cannabinoid effects may not be mediated by either CB1 or CB2 receptors. In some cases there is evidence that additional receptors, such as presynaptic site on glutamatergic terminals in the hippocampus mediating inhibition of glutamate release, may be involved (Katona et al., J. Neurosci., 2001). For instance, anandamide, an endogenous agonist ligand of the Cannabinoid receptor 1, and 2-AG 15, 16 CB1 receptors, which were found to be expressed at high levels in certain areas of amygdala and in ACC, were thought to be involved. Evidence followed confirming the presence of the endocannabinoid system in the hippocampus, cerebellum and presynaptic axon terminals including GABAergic interneurons. This intricate neurotransmitter system may play a role in various disorders from metabolic syndrome to multiple sclerosis.

In addition to maintaining the neuronal inhibition/excitation in balance, the endocannabinoid system may be involved in neuroprotection against acute and chronic inflammation forms. Presence of inflammation can be seen in autism. For instance, in brain specimen of autistic individual, the immunocytochemical studies showed marked activation of microglia and astroglia, and cytokine profiling indicated that macrophage chemoattractant protein (MCP)-1 and tumor growth factor-beta1, derived from neuroglia, were the most prevalent cytokines in brain tissues. Furthermore, examination of cerebrospinal fluid revealed a unique proinflammatory profile of cytokines, including a marked increase in MCP-1 . These findings may indicate that innate neuroimmune reactions play a pathogenic role in an undefined proportion of autistic patients.

The endocannabinoid system may further play an important role in neuroprotection both in acute neuronal injury and in chronic neurodegenerative disorders. Multiple mechanisms have been implicated, such as modulation of excitatory glutamatergic transmissions and synaptic plasticity via presynaptic CB1 receptors. A second pathway may implicate modulation of immune responses and the release of inflammatory mediators instigated by the stimulation of CB1, CB2 and non CB1/CB2 receptors on neurons, astrocytes, microglia, macrophages, neutrophils and lymphocytes and antioxidant properties of cannabinoids. In some instances, excitotoxicity, the toxic effect due to the overactivation of glutamate receptors and the resulting oxidative stress may contribute to the pathological processes eventually leading to cellular dysfunction or death in both acute and chronic forms of neurodegeneration. Studies in mice have shown that anandamide and synthetic agonists of CB1 receptors protected the newborn murine brain against excitotoxic damage, showing the importance of functional endocannabinoid system in early life neuronal insults.

The endocoannabinoid system may also be involved in mental disorders such as schizophrenia and anxiety. For example, postmortem radioligand studies showed increased CB1 receptor density in dorsolateral and anterior cingular regions and subregions of the prefrontal cortex in schizophrenia. Furthermore, levels of anandamide may be increased in cerebrospinal fluid and blood from schizophrenic patients. The high level of CB1 receptors in the hippocampus, amygdalae, prefrontal and anterior cingular cortex, which can be key regions in the regulation of anxiety, suggests that the endocannabinoid system plays a role in the control of anxiety (Herkenham et al., P.N.A.S., 1990; Glass et al., Neuroscience, 1997).

Brain areas that may be involved in autism such as amygdalae, hippocampus, ACC and others are also areas where endocannabinoid CB1 receptors may be abundant. In children with autism, functional MRI studies showed weak connectivity between amygdalae and temporal lobe (i.e., a pathway involved in the identification of facial expressions).

The amygdala in relation to the orbital frontal area and the hippocampus with the prefrontal area has been considered to be abnormal as well in autism (Loveland et al., Neuropsychologia, 2008; Schlkin J. Brain Gogn., 2007). EEG studies have revealed findings consistent with general GABA inhibitory neurotransmitter deficiency resulting in reduced number and/or strength of thalamo-cortical connections in autistic subjects (Thatcher et al., 2009).

Endocannabinoid system also shown to be involved in learning which is significantly abnormal in autistic disorders (Campolongo et al. P.N.A.S, 2009; Solinas et al., Br. J. Pharmacol., 2008; Abush & Akirav, Hippocampus, 2009; Reich et al., J. Psychopharmacol., 2008). Even though the possibility of endocannabinoid dysregulation has never been tested in autism per se, CB1 receptor genetic variations in individual differences in social responsivity has been postulated (Chakrabarti et al., 2006; Moreira & Lutz, 2008).

As such, core clinical manifestations of autism, in one embodiment, may be due to dysfunction of endocannabinoid system from an early overwhelming acute inflammatory insult in genetically predisposed children, followed by the development of excitotoxicity and continued dysfunction of endocannabinoid system causing imbalance between the inhibitory and excitatory GABAergic and glutamatergic systems in different parts of the brain. In another embodiment, manipulation of endocannabinoid function, and restoration of excitation/inhibition balance between GABAergic-glutamate systems may improve, alleviate, or reverse the core findings of autism, especially if introduced before excitotoxic neuron damage.

In accordance with an embodiment of the present invention, a composition having an endocannabinoid agonist-antagonist effect may be used to treat, prevent, alleviate, reduce or ameliorate symptoms associated with Pervasive Developmental Disorder, such as Autism, Asperger disorder and/or Retts disorder by restoring a balance between inhibitory GABAergic pathways and excitatory glutamatergic pathways. Some aspects of the invention relate to nutraceutical compositions or dietary supplements used to improve, support or enhances neurological function or behavioral symptoms associated with Pervasive Developmental Disorders. In some embodiments, nutraceutical compositions may alleviate, treat, or reverse symptoms that may not improve by conventional drug treatment and/or behavioral therapy. In some aspects of the invention, the composition may be used as a nutritional supplement for people who may need to improve neurological function. In one embodiment, the composition may include a therapeutically effective amount of passion flower extract. The passion flower extract may be selected from one of *passiflora incarnate* extract, *passiflora coerulea* extract, *passiflora edulis* and combinations thereof. The composition may further include a therapeutically effective amount of one of magnesium chloride, vitamin B6, and Coenzyme Q10 (CoQ10) and combinations thereof.

Pervasive Developmental Disorders (PDD) refers to a group of disorders characterized by delays in the development of multiple basic functions including socialization and communication. Pervasive Developmental Disorders include autism, a developmental brain disorder characterized by impaired social interaction and communication skills, and limited range of activities and interests. Autism is the most characteristic and best studied PDD. Other disorders associated with PDD include Asperger syndrome, Rett syndrome, and Childhood Disintegrative Disorder (CDD). Symptoms of PDD may include communication problems such as, but not limited to, difficulty using and understanding language, difficulty relating to people, objects, and events, unusual play with toys and other objects, difficulty with changes in routine or familiar surroundings, and repetitive body movements or behavior patterns, such as hand flapping, hair twirling, foot tapping, or more complex movements.

In some embodiments, the composition of the present invention may be used to prevent, alleviate, reduce, treat or ameliorate symptoms associated with a Pervasive Developmental Disorder. In some embodiments, the composition of the present invention supports, promotes, and maintains healthy neurological health in autistic individuals or in subjects diagnosed with Pervasive Developmental Disorder.

In one embodiment, the composition of the present invention may be used as a drug for preventing, alleviating, reducing, treating or ameliorating symptoms associated with a Pervasive Developmental Disorder. A drug, in general, is a substance that, when absorbed into the body of a living organism, alters normal bodily function. As used in pharmacology, a drug is a chemical substance used in the treatment, cure, prevention, or diagnosis of disease or used to otherwise enhance physical or mental well-being. Drugs may be used for a limited duration, or on a regular basis for chronic disorders.

In another embodiment, the composition of the present invention may be used as a food supplement for enhancing a person's natural well-being and health. As used herein, a food supplement, also known as dietary supplement or nutritional supplement, is a preparation intended to supplement the diet and provide nutrients, such as vitamins, minerals, fiber, fatty acids, or amino acids, that may be missing or may not be consumed in sufficient quantity in a person's diet.

The composition of the present invention, in another embodiment, may be used as a medical food for the dietary management of a disease or disorder, such as a Pervasive Developmental Disorder. Medical foods are used to manage diseases or disorders that have distinctive nutritional needs that cannot be met by normal diet alone. Medical foods are distinct from the broader category of foods for special dietary use and from traditional foods that bear a health claim. In order to be considered a medical food, the product must be a food for oral ingestion or tube feeding, be labeled for the dietary management of a specific medical disorder, disease or condition for which there are distinctive nutritional requirements, and be intended to be used under medical supervision.

The composition of the present invention, in another embodiment, may be used as a meturacitical. The term "nutraceutical" as used herein denotes usefulness in both nutritional and pharmaceutical fields of application. Thus, novel nutraceutical compositions can be used as supplements to food and beverages and as pharmaceutical formulations for enteral or parenteral application which may be solid formulations, such as capsules or tablets, or liquid formulations, such as solutions or suspensions.

Passion Flower Extract

In accordance with an embodiment of the present invention, the composition may include a passion flower extract having an endocannabinoid agonist-antagonist effect to restore a balance between inhibitory GABAergic pathways and excitatory glutamatergic pathways. Passion flowers are plants that possess natural endocannabinoid agonist-antagonist effects and GABAergic and possible anti-inflammatory effects and may be used to target implicated pathogenetic pathways in autistic spectrum disorder.

In one embodiment, the passion flower may be *passiflora incarnate*. *Passiflora incarnata* is an herbal supplement having reduced side effects as well as affects GABAergic and endocannabinoid neurotransmitter systems. *Passiflora incarnata* is a native to tropical America and has been used as an anxiolytic and sedative for centuries (Dhawan et al., J. Med. Food, 2001). Pharmacological studies suggest that *Passiflora incarnata* may have anxiolytic and sedative effects. *Passiflora incarnata* may be used in the treatment of marijuana addiction and withdrawal. One study reports evaluation of the benzoflavone moiety from the plant *Passiflora incarnata* in the treatment of cannabis addiction. The benzoflavone moiety of *Passiflora incarnate*, when administered concurrently with delta9-THC, prevented the development of tolerance and dependence of cannabinoids in mice. Even an acute administration of the benzoflavone moiety significantly blocked the expression of withdrawal effects in delta9-THC-dependent mice (Dhawan et al. J. Pharm. Pharmacol., 2002). The plant may act as agonist-antogonist on the endocannabinoid system.

*Passiflora incarnata* may include active components known as flavonoids or bioflavonoids, collectively known as Vitamin P and citrin. Flavonoids may have anti-inflammatory, antioxidant and anxiolytic effects. These effects may take place via GABA-mediated pathways. Examples of flavinoids include, but are not limited to, Alpha-alanine, Apigenin, D-fructose, D-glucose, Flovonoids, Gum, Gynocardin, Harmaline, Harmolol, Harmine, Harmol, Homoorientin, Isoorientin, Isovitexin, Kaempferol, Lutenin-2, Luteolin, Maltol, N-nonacosane, Orientin, Passiflorine, Phenylalanine, Proline, Quercetin, Raffinose, Rutin, Saccharose, Saponaretin, Saponarine, Scopoletin, Sitosterol, Stigmasterol, Sucrose, Tyrosine, Umbelliferone, Valine, and Vitexin.

In an embodiment of the present invention, the composition may include a Passion flower extract. As used throughout the specification and claims, the term Passion flower extract is intended to be used broadly, and can encompass plant extracts made by conventional means, such as steam distillation, water-based extractions, alcohol-based extractions, or organic solvent-based extractions (e.g. water, alcohol, ethyl acetate), such as ethyl acetate, and ion-exchange chromatography.

Of course, it should be noted that the present invention is not limited to the use of *passiflora incarnate*. Examples of other passion flowers include, but are not limited to, *passiflora coerulea* and *passiflora edulis*. The passion flower extract may be made from any species of the genus *passiflora*, such as *passiflora incarnata, passiflora coerulea* and *passiflora edulis* and combinations thereof.

In some embodiments, the composition may include from about 10 mg to about 500 mg of Passion flower extract per dosage form. The passion flower extract may be selected from one of *passiflora incarnata* extract, *passiflora coerulea* extract, *passiflora edulis* and combinations thereof. In an embodiment, *passiflora incarnata* extract may be present from about 100 mg to about 500 mg. In another embodiment, *passiflora coerulea* extract may be present from about 50 mg to about 400 mg. In another embodiment, *passiflora edulis* extract may be present from about 10 mg to about 200 mg. In some embodiments, the passion flower extract contain flavanoisds as well as other compounds that may also be bioactive, and/or increase the bioavailability of the active components of Passion flower. In an embodiment, a combination of *passiflora* extracts may be included in the composition. In an embodiment, one of more flavonoids may be included in the composition. Of course, if desired, other dosages such as those above and below the noted ranges may also be suitable.

Magnesium (Magnesium Chloride)

In accordance with an embodiment of the present invention, the composition may include magnesium. Magnesium (Mg) is an oil-soluble substance and is the fourth most abundant mineral in the body. Approximately 50% of total body magnesium is found in bone. The other half is found predominantly inside cells of body tissues and organs. Only 1% of magnesium is found in blood, but the body works very hard to keep blood levels of magnesium constant.

Magnesium is needed for more than 300 biochemical reactions in the body as it activates 76 percent of the enzymes in the body. Magnesium helps maintain normal muscle and nerve function, keeps heart rhythm steady, supports a healthy immune system, and keeps bones strong. A lack of magnesium, on the other hand, may inhibit nerve cell communication, which can lead to cell excitability. Magnesium also helps regulate blood sugar levels, promote normal blood pressure, and is known to be involved in energy metabolism and protein synthesis. Magnesium may further play a role in preventing and managing disorders such as hypertension, cardiovascular disease, and diabetes. Dietary magnesium is absorbed in the small intestines and excreted through the kidneys.

In an embodiment of the present invention, the composition may include magnesium. The composition may include from about 20 mg to about 200 mg of magnesium chloride per dosage form. Of course, other dosages such as those above and below the noted ranges may also be suitable.

Co Enzyme Q10 (CoQ10)

In an embodiment, the composition of the present invention may further include Co Enzyme Q10, or CoQ10. CoQ10, or ubiquinone, is a naturally occurring compound found in nearly every cell in the body. CoQ10 plays a key role in producing energy in the mitochondria, the part of a cell responsible for the production of energy, in the form of ATP. In each human cell, food energy is converted into energy in the mitochondria with the aid of CoQ10. Ninety-five percent of all the human body's energy requirements (ATP) are converted with the aid of CoQ10. Therefore, those organs with the highest energy requirements, such as the heart, the lungs, and the liver have the highest CoQ10 concentrations. CoQ10 is used by cells to produce energy needed for cell growth and maintenance. CoQ10 is also used by the body as an antioxidant.

Benefits of CoQ10 include, but are not limited to, improved efficiency of cellular energy production, increased energy, enhanced immune system strength, reduction of high blood pressure, improved and sometimes reversed periodontal disease, improved efficacy of weight loss programs, and reduced side effects from chemotherapy. CoQ10 may also increase intrinsic strength of the heart muscle. and may be used to treat congestive heart failure, cardiac arrhythmia, ischemic injury and angina pectoris. CoQ10 may further be effective in lowering blood pressure and reducing ischemic and hypoxic injury. Additionally, CoQ10 may act as an immunologic stimulant and a potent antioxidant as well as aiding in detoxification.

In an embodiment, the composition may include CoQ10. The composition may include from about 5 mg to about 100 mg of CoQ10 per dosage form. Of course, if desired, other dosages such as those above and below the noted ranges may also be suitable as the present invention is not intended to be limited in this manner.

Vitamin B6

The composition of the present invention may, in another embodiment, include Vitamin B6. Vitamin B6 (pyridoxine) is a water-soluble compound and is an essential vitamin that is necessary for more than 60 biological processes in a healthy human body. The body converts vitamin B6 into pyroxidal-5-phosphate (PLP), an enzyme that is used to release energy from starches and break down proteins. PLP is also used in the production of important chemicals in the brain.

In an embodiment, the composition may include Vitamin B6. The composition may include from about 10 mg to about 50 mg of Vitamin B6 per dosage form. Of course, other dosages such as those above and below the noted ranges may also be acceptable.

Compositions and Formulations

The herb-based composition of the present invention can be used in beverages, tonics, infusions, or food-stuffs alone, or in combination with other dietary supplements or therapeutics. The herb-based composition of the present invention can be used alone or further formulated with pharmaceutically acceptable compounds, vehicles, or adjuvants with a favorable delivery profile, i.e., suitable for delivery to a subject. Such compositions typically comprise the herb-based composition of the present invention and a pharmaceutically acceptable carrier. As used herein, "pharmaceutically acceptable carrier" is intended to include any and all solvents, dispersion media, coatings, antibacterial and antifungal compounds, isotonic and absorption delaying compounds, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non aqueous vehicles such as fixed oils may also be used. The use of such media and compounds for pharmaceutically active substances is well known in the art. Except insofar as any conventional media or compound is incompatible with the active compound, use thereof in the compositions is contemplated. Supplementary active compounds can also be incorporated into the compositions.

A composition of the present invention may be formulated to be compatible with its intended route of administration. Examples of routes of administration include oral, buccal, injectable, intravenous, intraperitoneal, subcutaneous, inhalational, intramuscular, intraarticular, intraarterial, intracerebral, intracerebellar, intrabronchial, intrathecal, parenteral, rectal, sublingual, topical, transdermal, and aerosol route. The pH can be adjusted with acids or bases, such as hydrochloric acid or sodium hydroxide.

Oral compositions generally include an inert diluent or an edible carrier. They can be enclosed in gelatin capsules, caplets compressed into tablets, chewable tablets, quick dissolve tablets, effervescent tablets, reconstitutable powders, elixirs, liquids, solutions, suspensions, emulsions, tablets, multi-layer tablets, bi-layer tablets, capsules, soft gelatin capsules, hard gelatin capsules, caplets, gummie, lozenges, chewable lozenges, beads, powders, granules, particles, microparticles, dispersible granules, cachets, douches, suppositories, creams, topicals, inhalants, aerosol inhalants, patches, particle inhalants, implants, depot implants, ingestibles, injectables, infusions, health bars, confections, animal feeds, cereals, yogurts, cereal coatings, foods, nutritive foods, functional foods and combinations thereof. Oral compositions can also be prepared using a fluid carrier for use as a mouthwash, wherein the compound in the fluid carrier is applied orally and swished and expectorated or swallowed.

Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or sterotes; a glidant such as colloidal silicon dioxide; a sweetening compound such as sucrose or saccharin; or a flavoring compound such as peppermint, methyl salicylate, or orange flavoring.

The following procedures represent, without limitation, acceptable methods of preparing formulations falling within the scope of the inventive subject matter.

Quick dissolve tablets may be prepared, for example, without limitation, by mixing the formulation with agents such as sugars and cellulose derivatives, which promote dissolution or disintegration of the resultant tablet after oral administration, usually within 30 seconds.

Soft gel or soft gelatin capsules may be prepared, for example, without limitation, by dispersing the formulation in an appropriate vehicle (vegetable oils are commonly used) to form a high viscosity mixture. This mixture is then encapsulated with a gelatin based film using technology and machinery known to those in the soft gel industry. The industrial units so formed are then dried to constant weight.

Chewable tablets, for example, without limitation, may be prepared by mixing the formulations with excipients designed to form a relatively soft, flavored, tablet dosage form that is intended to be chewed rather than swallowed. Conventional tablet machinery and procedures, that is both direct compression and granulation, i.e., or slugging, before compression, can be utilized. Those individuals involved in pharmaceutical solid dosage form production are well versed in the processes and the machinery used as the chewable dosage form is a very common dosage form in the pharmaceutical industry.

Film coated tablets, for example, without limitation, may be prepared by coating tablets using techniques such as rotating pan coating methods or air suspension methods to deposit a contiguous film layer on a tablet. This procedure is often done to improve the aesthetic appearance of tablets, but may also be done to improve the swallowing of tablets, or to mask an obnoxious odor or taste, or to improve the usual properties of an unsightly uncoated tablet.

Compressed tablets, for example, without limitation, may be prepared by mixing the formulation with excipients intended to add binding qualities to disintegration qualities. The mixture is either directly compressed or granulated then compressed using methods and machinery quite well known to those in the industry. The resultant compressed tablet dosage units are then packaged according to market need, i.e., unit dose, rolls, bulk bottles, blister packs, etc.

The herb-based composition of the present invention can also be prepared as compositions in the form of suppositories (e.g., with conventional suppository bases such as cocoa butter and other glycerides) or retention enemas for rectal delivery.

In one embodiment, the herb-based composition of the present invention are prepared with carriers that will protect the compound against rapid elimination from the body, such as, without limitation, controlled release, immediate release, extended release, pulse release, variable release, controlled release, timed release, sustained release, delayed release, long acting, and combinations thereof. As used herein, a "controlled release form" means any form having at least one component formulated for controlled release. As used herein, "immediate release form" means any form having all its components formulated for immediate release. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention may be dictated by and directly dependent on the unique characteristics of the herb-based composition and the particular therapeutic effect to be achieved, and the limitations inherent in the art of compounding such an active compound for the treatment of individuals. The compositions can be included in a container, pack, or dispenser together with instructions for administration.

The composition of the present inventive subject matter may be administered in a partial, i.e., fractional dose, one or more times during a 24 hour period, a single dose during a 24 hour period of time, than a double dose during a 24 hour period of time, or more an a double dose during a 24 hour period of time. Fractional, double or other multiple doses may be taken simultaneously or at different times during the 24 hour period. The doses may be uneven doses with regard to one another or with regard to the individual components at different administration times. For example, without limitation, the amount of calcium in a morning dose is different from the amount of calcium in an evening dose.

EXAMPLES

Example 1

Diagnosis of autism or autistic spectrum disorder is determined by consensus diagnosis including the results of the Autism Diagnostic Interview-Revised (ADI-R) completed by a research-reliable ADI-R rater and integrated with all available clinical information. Patients with allergy to passion flower, or having severe seizure disorder or any medical condition or behavioral difficulty that would prohibit treatment are excluded from the study. Highly purified specially formulated passion flower extract is used in this study.

Patients (age ranging from 4 year old to 22 year old) are treated with a starting dose of 250 mg twice a day. Dosing can be adjusted and changed depending on clinical response every week, in increments of 250 mg, up to 25 mg/lb.

Baseline Vineland adaptive behavior scale, routine comprehensive metabolic panel (Na,K, Cl, HCO3, Ca, creatinine, BUN, ALT, AST), an ECG, vital signs height, weight, blood pressure, heart rate), clinical global scale (CGI-S), social responsiveness scale, and aberrant behavior checklist are recorded at baseline and at the end of the treatment (e.g. 12 weeks).

Additional assessments of effectiveness include: Irritability Subscale of the Aberrant Behavior Checklist (ABC) and other ABC subscales at end of treatment compared with baseline; the Nisonger Child Behavior Rating Form (N-CBRF); the Visual Analogue Scale (VAS), a measure of the patient's most disturbing symptom; and the Clinical Global Impression (CGI) of the overall severity of the disorder.

The CGI-S is rated by a clinician and the Irritability subscale of the aberrant behavior checklist (ABC-I) is rated by the parent at baseline and four week intervals across the first 12 weeks of the study and again at week 24.

The CMP, ECG, and vital signs, are repeated at the end of the study (e.g. 12 weeks). All behavioral and medical parameters are recorded at the end of 24 weeks following 12 weeks in the crossover period. Adverse reaction are monitored and recorded.

Effect of passion flower on the irritability score is evaluated. It is proposed that active supplementation lowers irritability score by 25% after 10 weeks of treatment.

Example 2

Two patients diagnosed with Pervasive Developmental Disorder (PDD) such as Asperger syndrome, or autism as well as disorders associated with Pervasive Developmental Disorder such as ADHD, impulsivity, Sensory Integration disorder, Emotional behavior disorder, were selected for the study. Patients (age ranging from about 5 to 8 years old) exhibited delays in the development of socialization and communication skills, repetitive movement, hyperactivity, focused interests, multiple daily temper tantrums, disturbed sleep pattern, anxiety, lack of self control and lack of empathy.

Patients were treated with a formulation comprising passion flower extract. The formulation (capsule) included a combination of 500 mg blend of purified of *Passiflora Incarnata* extract (400 mg); *Passiflora Coerulea* extract (90 mg) and *Passiflora Edulis* extract (10 mg).

A parent or caregiver evaluated the child's behavior and symptoms during the course of treatment. In both cases, parents reported improvements in personality, mood, self control, empathy, and social functioning, reduced sensitivity to sound, better sleep patterns, decreased aggressiveness, improved attention span and eye contact, lessened hyperactivity.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. A composition in unit dosage form for improving neurological function in Pervasive Developmental Disorder comprising:
   a pharmaceutical carrier;
   a therapeutic mixture containing a therapeutically effective amount of a combination of *Passiflora incarnata* extract, *Passiflora coerulea* extract, and *Passiflora edulis* extract; and
   one of magnesium, vitamin B6, Coenzyme Q, or combinations thereof.

2. The composition of claim 1, wherein the combination of *Passiflora incarnata* extract, *Passiflora coerulea* extract, and *Passiflora edulis* extract is present in an amount of from about 10 mg to about 500 mg per unit dosage form.

3. The composition of claim 1 wherein the *Passiflora incarnata* extract is present in an amount of from about 100 mg to about 500 mg per unit dosage form.

4. The composition of claim 2 wherein the unit dosage form is a gelatin capsule, tablet, chewable tablet, quick dissolve tablet, effervescent tablet, reconstitutable powder, multi-layer tablet, bi-layer tablet, capsule, soft gelatin capsule, hard gelatin capsule, caplet, gummie, lozenge, chewable lozenge, cachet, or suppository.

5. The composition of claim 2 wherein the *Passiflora coerulea* extract is present in an amount of from about 50 mg to about 400 mg and wherein the *Passiflora edulis* extract is present in an amount of from about 10 mg to about 200 mg.

6. The composition of claim 1 wherein the in the form of magnesium is magnesium chloride and the magnesium chloride is present in an amount of from about 20 mg to about 200 mg per unit dosage form.

7. The composition of claim 1 wherein vitamin B6 is present in an amount of from about 10 mg to about 50 mg per unit dosage form.

8. The composition of claim 1 wherein coenzyme Q10 is present in an amount of from about 5 mg to about 100 mg per unit dosage form.

9. The composition of claim 1 wherein the composition is a drug, a food supplement, a medical food, or a nutraceutical composition.

10. A method for reducing, ameliorating, treating, or alleviating symptoms associated with Pervasive Developmental Disorder in a subject suffering therefrom, comprising administering to said subject an effective amount of the composition according to claim 1.

11. The method of claim 10 wherein said administering comprises administering the composition orally, topically, intravenously, or by a combination thereof.

12. The method of claim 10 wherein said administering comprises administering the composition at a frequency in the range from about one a day to up to eight times or more a day.

13. The method of claim 10 wherein the Pervasive Developmental Disorder is one of autism, Asperger disorder or Retts disorder.

14. A composition in unit dosage form for improving neurological function in Pervasive Developmental Disorder comprising:

a pharmaceutical carrier;

a therapeutic mixture consisting of a therapeutically effective amount of a combination of *Passiflora incarnata* extract, *Passiflora coerulea* extract, and *Passiflora edulis* extract; and one of magnesium, vitamin B6, Coenzyme Q, or combinations thereof.

15. A composition in unit dosage form for improving neurological function in Pervasive Developmental Disorder comprising:

a pharmaceutical carrier;

a therapeutic mixture containing a therapeutically effective amount of a combination of *Passiflora incarnata* extract, *Passiflora coerulea* extract, and *Passiflora edulis* extract, the combination consisting of 80% wt of *Passiflora incarnata* extract; 18% wt of *Passiflora coerulea* extract, and 2% wt of *Passiflora edulis* extract; and one of magnesium, vitamin B6, Coenzyme Q, or combinations thereof.

* * * * *